(12) United States Patent
Menon et al.

(10) Patent No.: US 6,863,121 B2
(45) Date of Patent: Mar. 8, 2005

(54) FLOW DISTRIBUTOR FOR AN ALKYLATION REACTOR OR HEAT EXCHANGER

(75) Inventors: Raghunath Gopal Menon, Katy, TX (US); Richard Addison Sanborn, Houston, TX (US); Raul Jasso Garcia, Sr., Houston, TX (US)

(73) Assignee: Shell Oil Company, Houston, TX (US)

( * ) Notice: Subject to any disclaimer, the term of this patent is extended or adjusted under 35 U.S.C. 154(b) by 269 days.

(21) Appl. No.: 10/123,767

(22) Filed: Apr. 16, 2002

(65) Prior Publication Data

US 2003/0192683 A1 Oct. 16, 2003

(51) Int. Cl.[7] .................................................. F28F 9/02
(52) U.S. Cl. ...................................... 165/158; 165/174
(58) Field of Search .................................. 165/158, 174

(56) References Cited

U.S. PATENT DOCUMENTS

| | | | | | |
|---|---|---|---|---|---|
| 3,306,351 | A | * | 2/1967 | Vollhardt | .................... 165/158 |
| 3,374,832 | A | * | 3/1968 | Tucker | ....................... 165/158 |
| 3,392,211 | A | * | 7/1968 | Markert et al. | ............. 165/158 |
| 4,078,292 | A | * | 3/1978 | Porter | ........................ 165/174 |
| 4,325,428 | A | * | 4/1982 | Schuurman | .................. 165/158 |
| 4,778,003 | A | * | 10/1988 | Helberg | ...................... 165/158 |
| 5,110,560 | A | * | 5/1992 | Presz et al. | ................. 165/174 |
| 5,531,266 | A | | 7/1996 | Ragi et al. | .................. 165/115 |
| 5,625,112 | A | | 4/1997 | Ragi et al. | .................. 585/709 |
| 5,811,625 | A | | 9/1998 | Ragi et al. | .................. 585/709 |
| 6,382,313 | B2 | * | 5/2002 | Mitsumoto et al. | ......... 165/174 |

OTHER PUBLICATIONS

Menon, R. G. and R. A. Sanborn, *Reactor Tube Bundle Flow Analysis*, Presented at Alky TechNet Meeting, Norco Refinery Complex, Dec. 6, 2000.

* cited by examiner

Primary Examiner—Leonard R. Leo

(57) ABSTRACT

The invention focuses on distributing the vapor/liquid flow that emerges from an inlet nozzle across the tube sheet of an alkylation reactor or heat exchanger. The flow distributor takes the two-phase flow that emerges from the inlet nozzle, turns it towards the tubesheet and delivers a uniform mixture across the tube sheet. The flow distributor is located in the channel head of the reactor or heat exchanger. In order to dislodge the liquid film from the wall of the inlet nozzle, trip rings and angular trip tabs are located internally in the flow distributor.

8 Claims, 7 Drawing Sheets

FLOW DISTRIBUTOR FOR AN ALKYLATION REACTOR OR HEAT EXCHANGER

BACKGROUND OF THE INVENTION

1. Field of the Invention

The invention is related to flow distributors for enhancing distribution of the reactor hydrocarbon effluent in the channel head of alkylation reactors to improve reactor refrigeration and to minimize tube fouling and corrosion. In the general case, the invention may be applied to improve the distribution of liquid in the channel head of any heat exchanger that has a combined liquid/vapor stream entering the channel head.

2. Description of Related Art

In the alkylation process, isobutane is reacted with light olefins in the presence of a sulfuric or hydrofluoric acid emulsion. Depending on the carbon number and isomer configuration of the olefin molecule, a branched chain isoparaffin results whose octane number ranges from the high 80's to 100. In the sulfuric acid process the reaction usually takes place at 40–50° F., requiring refrigeration.

A schematic of the process known to those skilled in the art is shown in FIG. 1 where liquid phase olefins 10 and isobutane 12 are continuously fed to the reactor 14 at about 40° F. An emulsion of immiscible hydrocarbon and sulfuric acid is formed in the reactor 14 by a mixing impeller 16. The impeller 16 also circulates the emulsion across chilling tubes (not shown) in the reactor 14. The emulsion is forced up from the reactor 14 through line 17 to a settler 18 where the hydrocarbon and acid phases separate. The acid is then returned to the reactor 14 by gravity through line 20. The hydrocarbon phase, which contains the motor alkylate, excess isobutane, propane and normal butane, is released from the settler 18 through line 19 to a flash valve 22 and proceeds into the inlet nozzle 23 of channel head 24 of the reactor 14. From the inlet nozzle 23 of channel head 24, the hydrocarbon vapor and liquid flows through the tube bundle 26 (see FIG. 2) which may comprise, e.g., 300 to 1000+ U-shaped tubes, and exits through outlet nozzle 25. Part of the excess isobutane and light hydrocarbon vaporizes as the reactor effluent flows through the U-tubes, thereby providing refrigeration to the process. The reactor effluent 30 goes to a flash drum 32. The vapor from flash drum 32 is compressed in compressor 34 and routed through chiller 36 and then via line 37a to separator 37. The propane rich stream 37c from separator 37 is fractionated in depropanizer column 38, with the LPG product stream 38a being purged from the unit. The liquid stream 35a from flash drum 32 is fractionated in deisobutanizer column 35. The bottoms alkylate 35c leaves the unit and is typically routed to gasoline blending. The normal butane side draw stream 35b also leaves the unit. The overhead stream 35d, rich in nonreacted isobutane, is combined with the isobutane-rich stream 37b from separator 37 and stream 38b from depropanizer column 38 and recycled to reactor 14.

The industry standard design for an alkylation reactor tube bundle assembly may comprise hundreds of U-shaped tubes. A typical channel head 24 with tube assembly 26 is shown in FIG. 2. A partition 24a in the channel head 24 separates the channel head into an inlet side 23a and an outlet side 25a. The reactor effluent vapor/liquid flow from flash valve 22 enters through an inlet nozzle 23 and proceeds into the inlet chamber 23a of channel head 24. There are several fundamental flaws with this design. The two-phase flow enters the inlet chamber 23a of channel head 24 with reasonably high velocity, since it has already begun to flash, and will impinge on the partition 24a. No provision is made for turning the incoming flow towards the tube sheet 24b on which the tube bundle 26 is mounted. Some of the flow will bend towards the inlet end of the U-shaped tubes (comprising tube bundle 26) that are attached to tube sheet 24b, and some will flow away from the tube sheet into the semi-elliptic head 24. The flow that circulates into the inlet side 23a of head 24 will curl back, pass around the rising inlet jet (from inlet nozzle 23) and enter the U-shaped tubes that are located on the outside, or periphery, of the tube bundle 26. Since the liquid phase is significantly more dense than the vapor phase, the bulk of the liquid will either turn towards the middle of the inlet tubes of tube sheet 24b or will impinge on the partition 24a. The vapor that curls back from the inlet side 23a of head 24 and flows through the outside tubes of tube bundle 26 is deficient in liquid and hence will have significantly lower heat transfer. Industry experience shows that problems with fouling and tube leaks are generally observed in the outside tubes, confirming the flow maldistribution.

Inventions incorporating internal vanes that divide the incoming stream into a plurality of streams have also been reported in the literature. (See U.S. Pat. Nos. 5,531,266, 5,625,112 and 5,811,625, the teachings of which are incorporated herein by reference.)

Division of the incoming stream into a plurality of streams has also been reported by the use of a cluster of small diameter tubes placed inside the channel head of the reactor.

The use of flow distributors as described herein to improve refrigeration and to increase tube bundle life through minimizing corrosion in alkylation processes has not been reported in the open literature.

This same device may be used to improve the distribution of liquid in a two-phase inlet stream on the tube sheet of any similarly configured heat exchanger channel head. When uniform vaporization of the incoming liquid fraction is desired in any of the various shell and tube heat exchangers, such as fixed tube sheet, U-tube, floating head, etc., the instant invention will promote said uniform distribution. The uniform distribution will enhance the vaporization of the liquid and the heat transfer in the exchanger.

SUMMARY OF THE INVENTION

A funnel-shaped flow distributor receives the vapor/liquid flow that emerges from an inlet nozzle to the channel head of an alkylation reactor and evenly distributes it across the tube sheet of the reactor. The flow distributor, placed in the reactor channel head, receives the two-phase flow that emerges from the inlet nozzle, turns it approximately 90 degrees toward the tube sheet, while allowing it to diverge, and delivers a relatively uniform mixture across the inlet side of the tube sheet and to the inlet of the tubes. A liquid film forms on the wall of the inlet nozzle and, in order to dislodge the liquid film, a trip ring is installed in the inlet of the flow distributor at the point where the flow distributor is attached to the inlet nozzle. In addition, slots, or windows, are cut into the bottom of the flow distributor around its circumference. The slots aspirate any liquid that may collect in the bottom of the channel head. A trip bar is installed inside the roof of the flow distributor, transverse to the direction of the fluid flow, to further disperse and distribute the liquid.

DESCRIPTION OF PREFERRED EMBODIMENTS

A major flaw of the industry standard design described above is that it does not address flow maldistribution across the tube sheet. The trend in the industry is to modify the tube inlet by using restriction orifices that will increase the pressure drop. While this will increase the liquid fraction in the flow, and possibly increase the liquid drop size, it will not significantly improve flow distribution. The industry trend of using tube inserts might, in fact, worsen the flow maldistribution by causing the complete segregation of the vapor and liquid phases.

Unlike inventions reported in the public domain, Applicants' invention does not require dividing the inlet stream into a plurality of streams by means of internal vanes or baffles. Internal vanes and baffles have to be welded inside the channel head and are, therefore, subject to breaking off and obstructing the inlet nozzle of the reactor. The design of the inlet device disclosed herein can also be broadly applied to improving flow distribution to tube bundle assemblies in general, including heat exchangers.

Applicants' invention is directed to an improvement of the alkylation reactors known in the prior art, such reactors also being sometimes referred to as the contactor. One of the major limitations in the alkylation process is the reactor temperature. Lowering the reactor temperature by increasing the overall heat transfer from the emulsion to the reactor effluent will allow significant increase in rates (and yield).

The overall heat transfer rate is, to a large extent, influenced by the degree of distribution of the vapor/liquid flow through the tubes comprising the tube bundle. Tubes that are liquid deficient, such as in the outside, or peripheral, tubes as known in the prior art, will have very low heat transfer rates. Therefore, a maldistributed liquid flow across the tube bundle will lead to significantly lower overall heat transfer. A maldistributed flow, where some of the tubes see minimal liquid and therefore run hotter, will also lead to accelerated tube corrosion and subsequently to tube leaks. Typical experience from alkylation units show that tube leaks are a major cause for unit shut downs and premature replacement of bundle assemblies.

Figure 1:
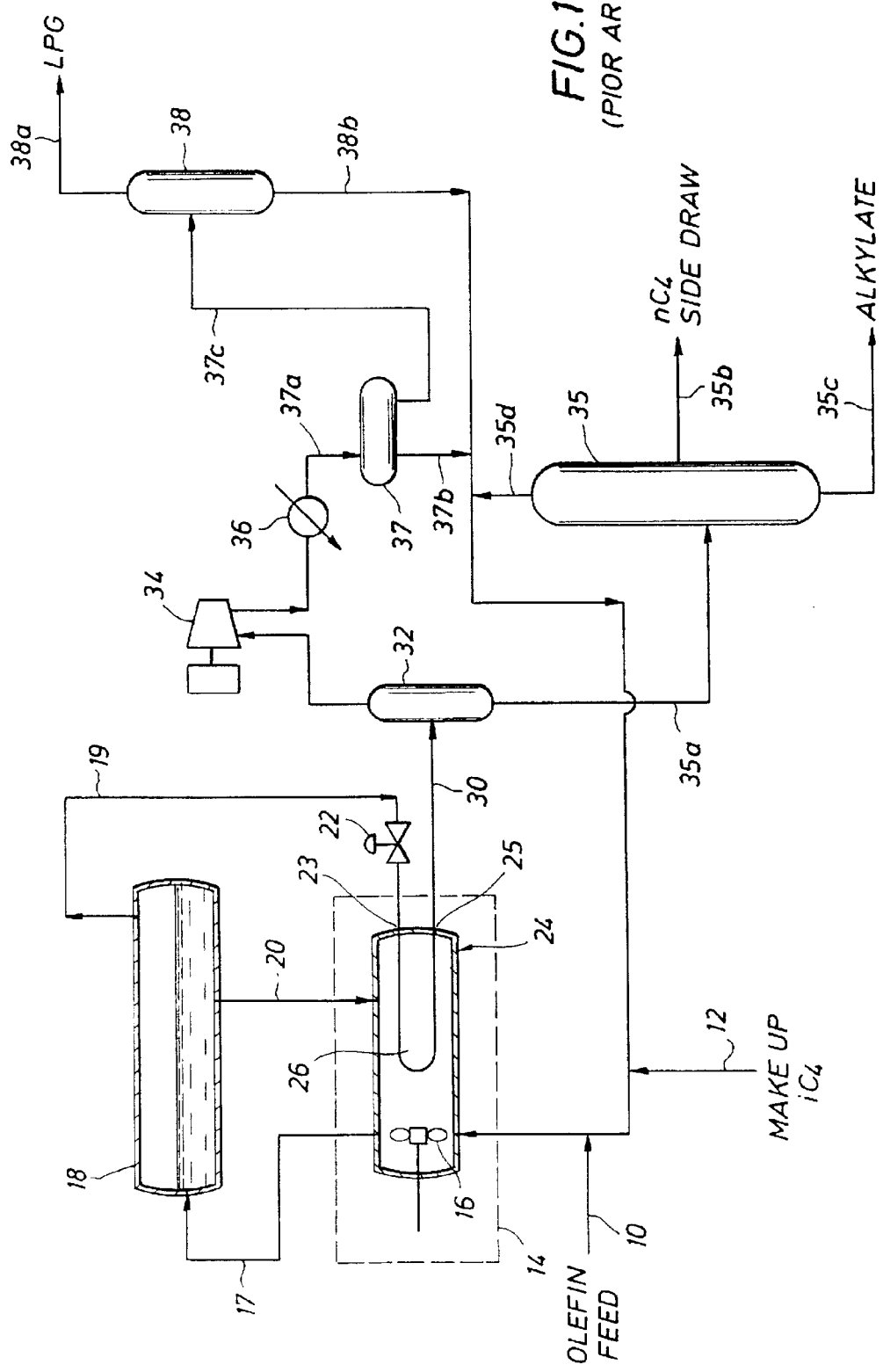
FIG. 1 is a schematic diagram of a typical alkylation unit process flow diagram of a prior art system.
Figure 2:
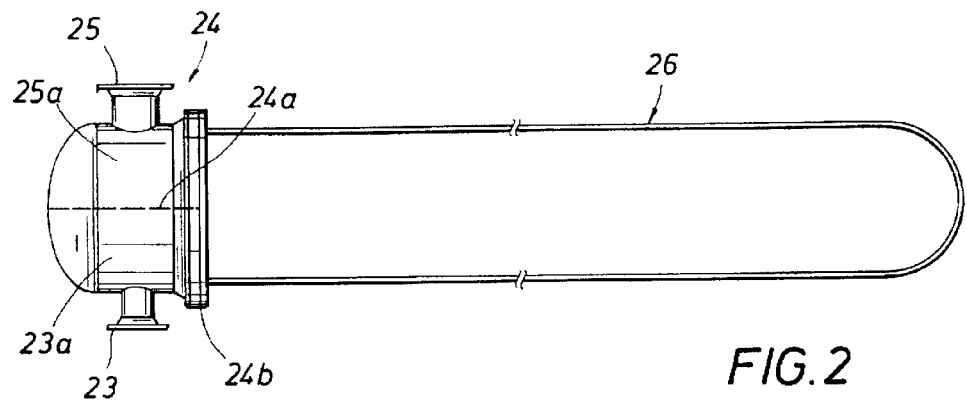
FIG. 2 is a cross-section of a typical industry standard design of a prior art alkylation reactor.
Figure 3A:
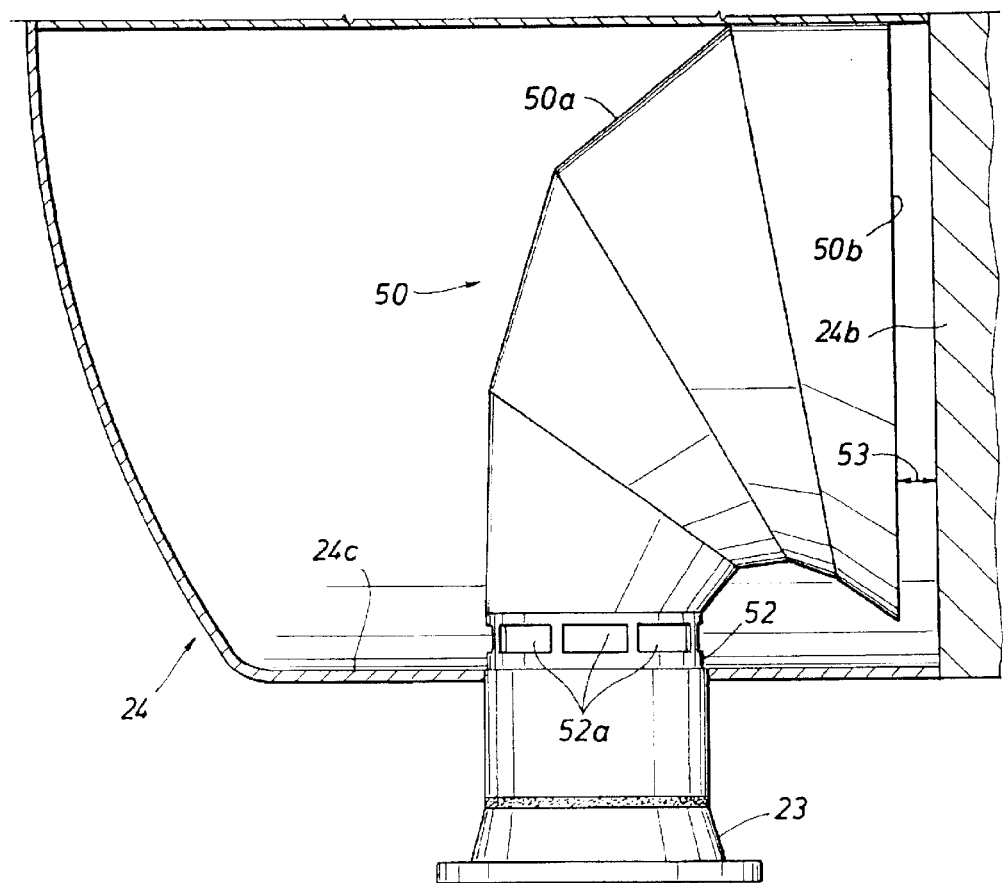
FIG. 3A is a side elevation sectional view of a flow distributor according to the instant invention.

The invention disclosed herein is directed to a method and apparatus for receiving the vapor/liquid flow that emerges from the inlet nozzle and uniformly distributing it across the inlet side of the tube sheet. This is accomplished by using a flow distributor 50 as shown in FIG. 3A. The flow distributor 50 is attached to the inlet nozzle 23 of the reactor channel head as shown in FIG. 3A. The flow distributor 50 is welded flush to the inlet nozzle 23 inside the channel head 24. The internal cross section of the flow distributor 50 is similar to that of a curved funnel and changes continually from that of the inlet nozzle 23, at its inlet, to that of the tube sheet 24b (shown without tube bundle 26 attached), at its discharge towards the tube sheet 24b as shown in FIG. 3A. The cross-sectional area change can be either smooth or mitered in several steps as shown in FIG. 3A. The flow distributor 50 receives the two-phase flow of reactor effluent that emerges from the inlet nozzle 23, turns it approximately 90 degrees while allowing it to diverge and delivers a uniform mixture across the inlet tubes (not shown) of the tube sheet 24b. A separation 53, on the order of $\frac{1}{16}$" to 3", is maintained between the face of the flow distributor 50 and the tube sheet 24b. This spacing 53 is required in order to allow communication of the vapor and liquid inside the horn with the remainder of channel head 24. Part of the purpose of this communication is to permit liquid that does not enter the tubes to be collected by aspiration through slots 52a, described in the following paragraph. In an alternative embodiment, shown in FIG. 3B, the face 50b of flow distributor 50 may be placed flush against the tube sheet 24b. In this embodiment it will be necessary to place drainage holes 50c and/or vents 50d in the flow distributor 50 for drainage of liquid that does not enter the tubes 26, as well as for communication of vapor with the remainder of the channel head.

Figure 3B:
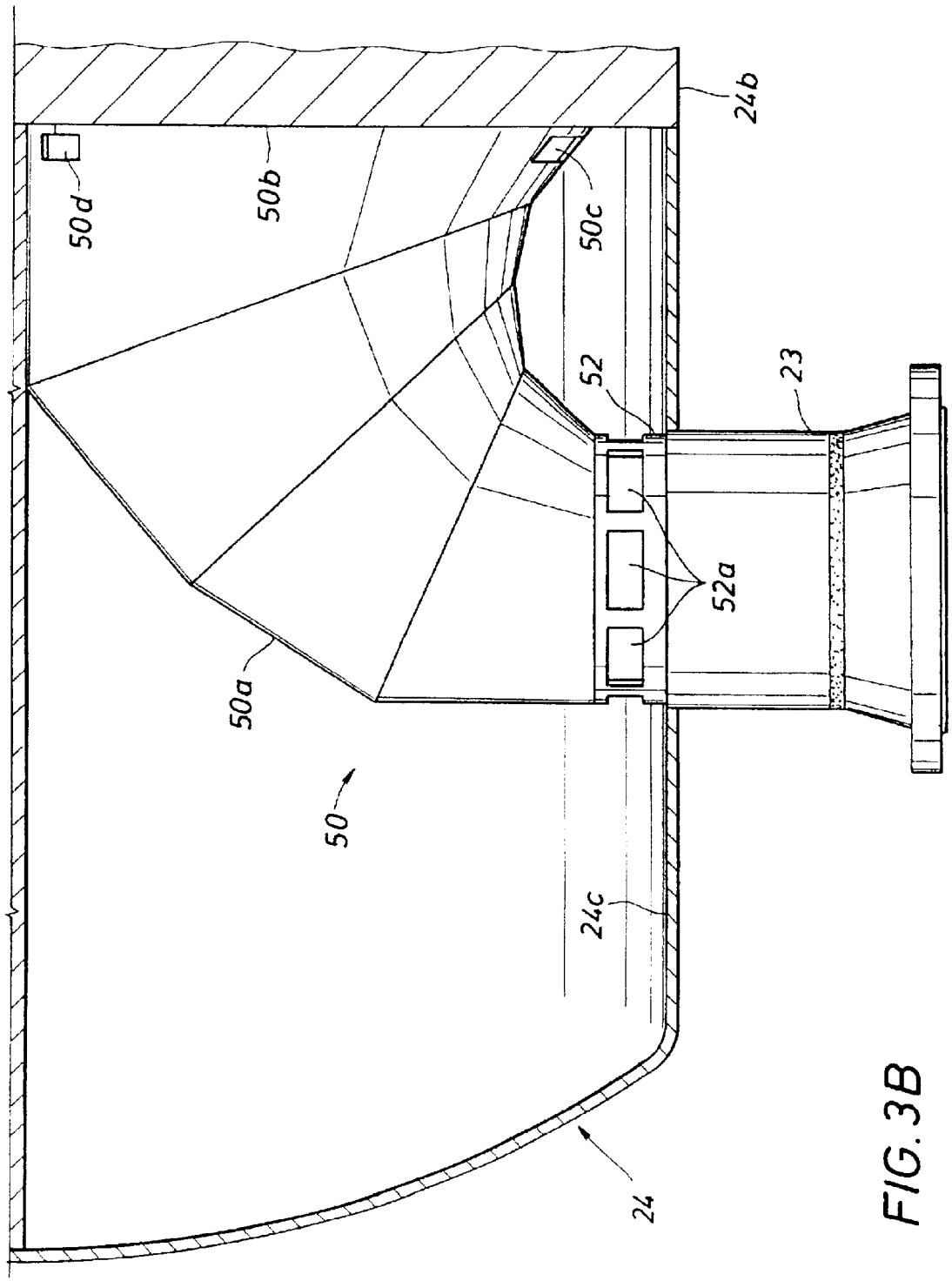
FIG. 3B is a side elevation sectional view of an alternate embodiment of a flow distributor according to the instant invention.
Figure 4A:
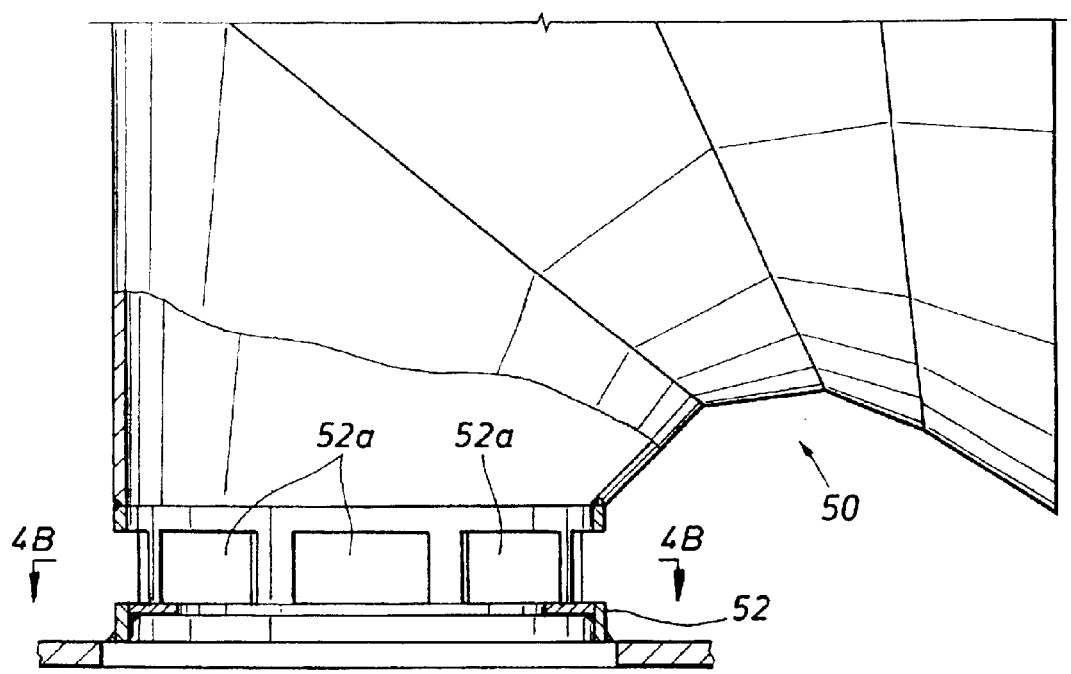
FIGS. 4A and 4B are sectional views showing the details of the trip ring and aspirator slots.
Figure 4B:
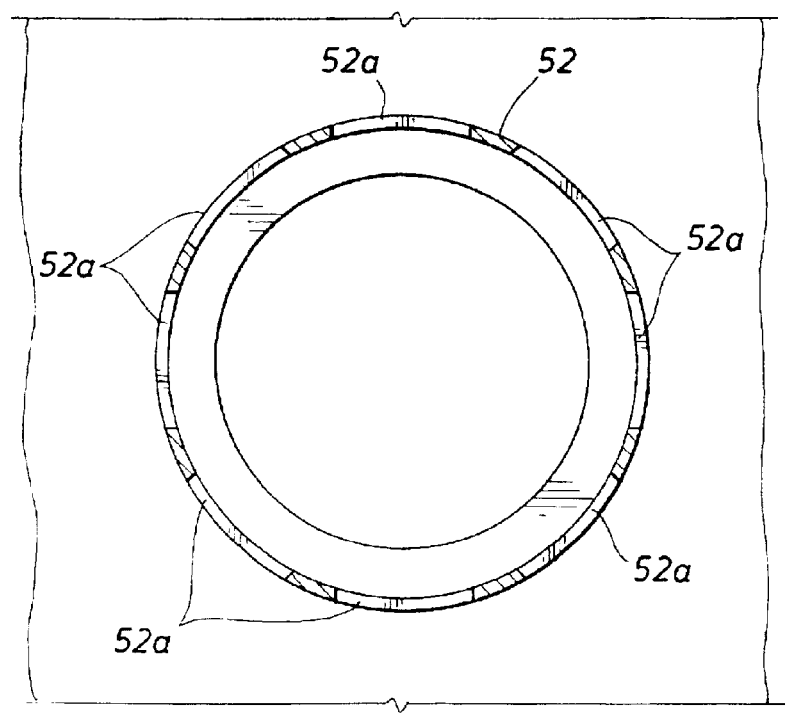

The flow that enters the channel head 24 through the inlet nozzle 23 is a mixture of vapor and liquid with a portion of the liquid being present as a film along the inside diameter of the inlet pipe and nozzle 23. A trip ring 52 is installed at the inlet of the flow distributor 50 as shown in FIGS. 3A and 3B and, in more detail, in FIG. 4A. The trip ring 52 dislodges the liquid film and helps to break up the film into drops that are subsequently transported by the vapor through the flow distributor 50. Slots (or windows) 52a are cut along and through the bottom (around the circumference) of the flow distributor 50 as shown in FIGS. 4A and 4B. The slots 52a are located immediately downstream of the trip ring 52. The "venturi" action of the trip ring 52 aspirates any liquid, that accumulates in the bottom 24c of the channel head 24, into the flow distributor 50 through the slots 52a, thereby further enhancing the distribution of the liquid phase.

Figure 5C:
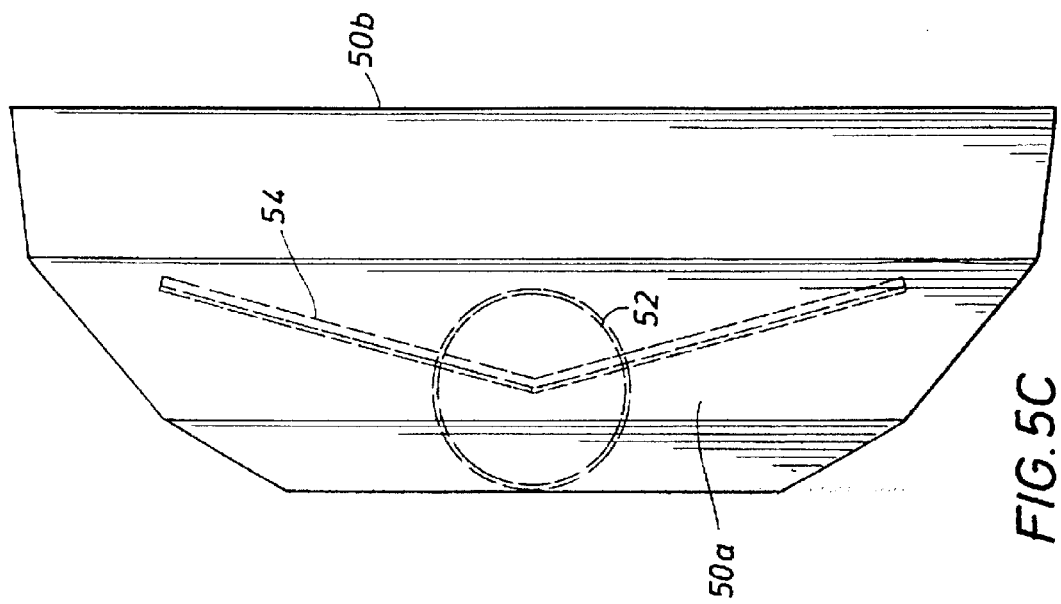
FIGS. 5A, 5B and 5C are elevational views of the flow distributor including the trip ring and angular trip bar.
Figure 5B:
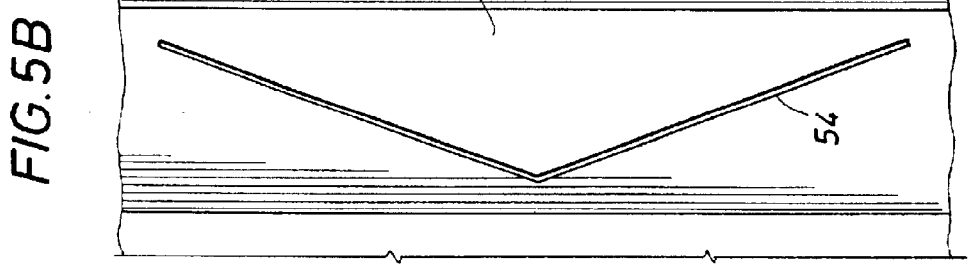
Figure 5A:
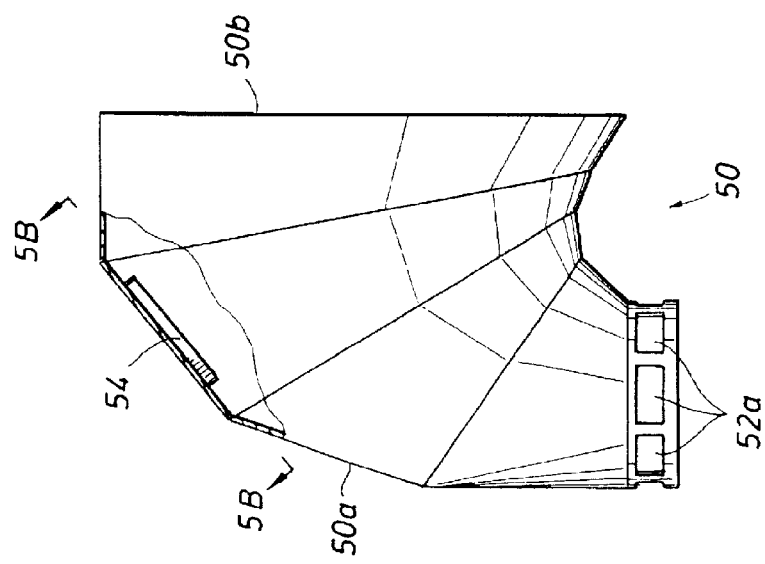

Referring now to FIGS. 5A–C, as the vapor/liquid mixture is turned approximately 90° by the contour of the distributor 50, a liquid film begins to develop on the inside of the roof 50a of the flow distributor 50. An angular trip bar 54, located in the roof of the distributor 50, serves to dislodge this liquid film resulting in drops and further improving the flow distribution.

FIGS. 5A–C show aspects of the flow distributor 50, trip ring 52 and trip bar 54. The trip bar 54 is installed on the roof 50a of flow distributor 50 at an angle of approximately 20–180 degrees, preferably 120 degrees, to the direction of flow. The trip bar 54 breaks up the liquid film on the roof 50a of the distributor 50 and enhances the uniformity of the liquid distribution. The trip bar 54 may include other embodiments such as separating the bar into discrete segments and individually installing each segment on the roof 50a. In still another embodiment, the trip bar may also be serrated with "grooves" or "notches" cut into the bar.

Figure 6A:
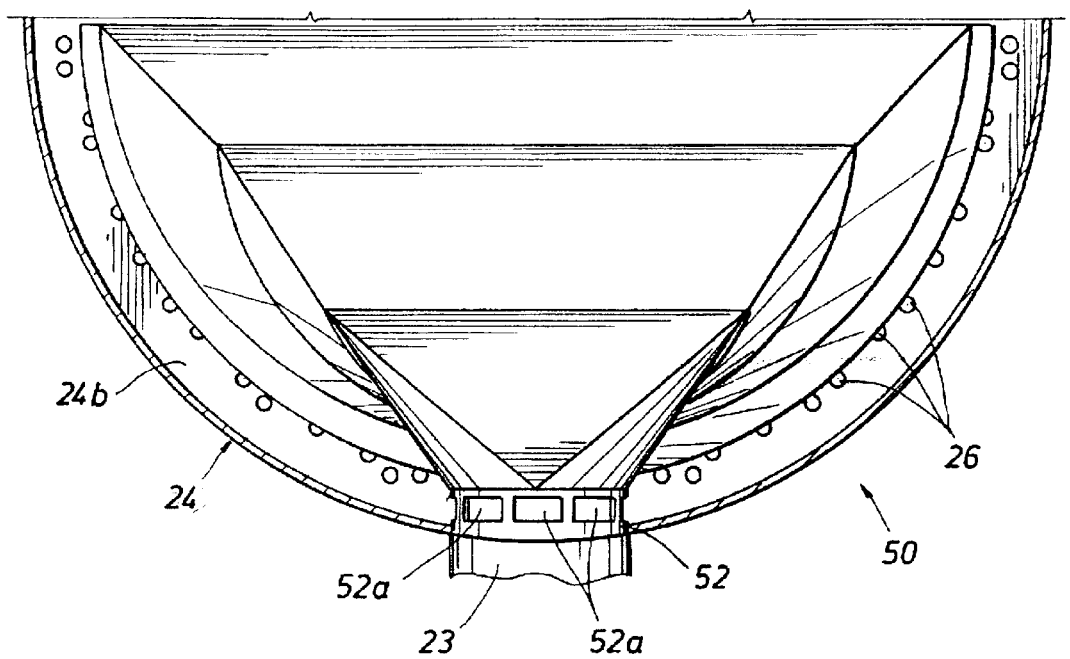
FIGS. 6A, 6B and 6C show rear, front and top views respectively of the flow distributor of FIG. 3.
Figure 6B:
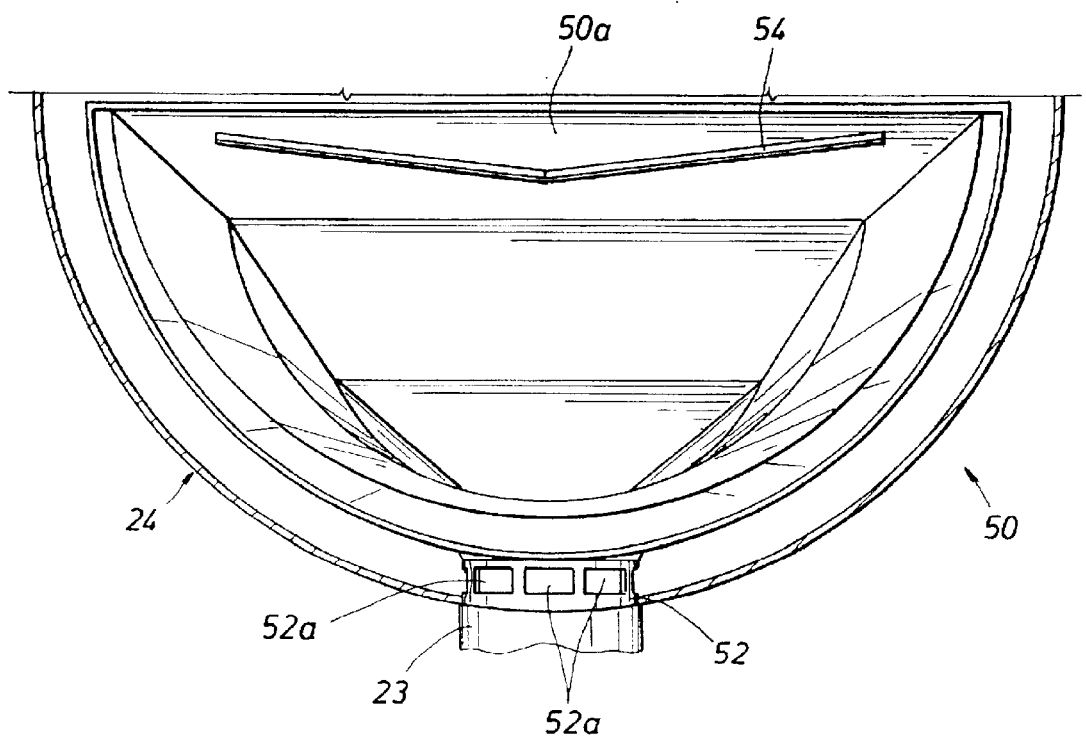
Figure 6C:
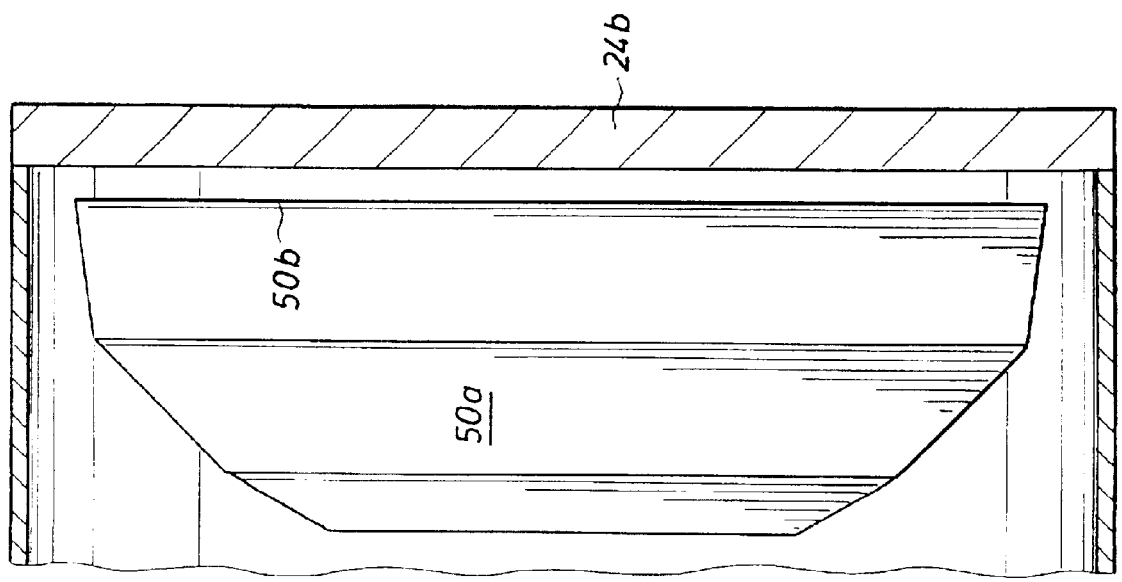

FIGS. 6A–C show rear, front and top views, respectively, of the distributor 50.

Applicants' invention significantly improves the distribution of vapor/liquid flow across the inlet tubes of a tube bundle 26 of alkylation reactors, compared to the industry standard. The distribution is accomplished by preventing the impingement of the inlet flow through inlet nozzle 23 onto the partition 24a. Instead, the flow distributor 50 changes the inlet flow direction by approximately 90 degrees while allowing expansion of the flow and directs it uniformly across the inlet side of the tube sheet 24a. The flow distributor 50 described herein does not rely on equally splitting the inlet flow into a plurality of streams. The improved flow distribution will allow the reactors to be operated at lower temperatures thereby increasing capacity and improving yield. In addition, better flow uniformity across the tube bundle 26 will minimize tube fouling and corrosion and, as a result, is expected to increase the life of the bundle assembly.

The flow distributor described above was developed using detailed two-phase flow computer simulations of the process and through testing of a scale model of a commercial alkylation reactor channel head.

Figure 7:
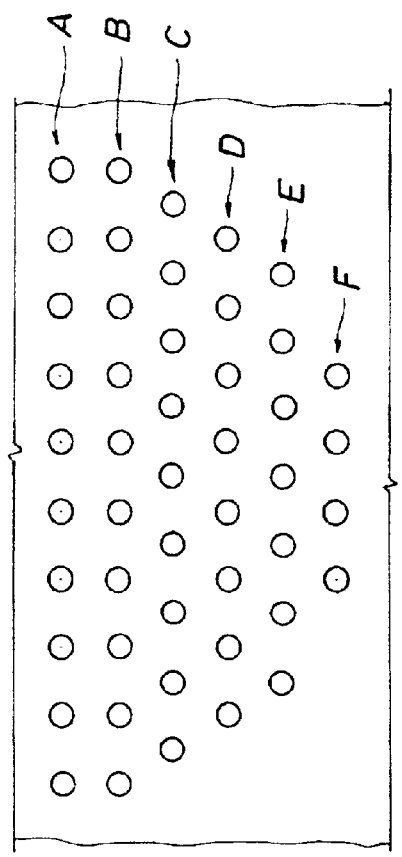
FIG. 7 is a schematic drawing of the tube sheet and tube configuration used for obtaining the data of Table 1.

FIG. 7 shows a tube sheet with the tube layout arrangement used to obtain the data of Table 1. The two-phase vapor/liquid flow into the channel head 24 and across the tube sheet was simulated for the existing design (prior art) and with the newly conceived flow distributor 50. A marked improvement in distribution of the flow across the tube bundle is seen with the current invention as shown in Table 1. The liquid distribution across the tube sheet was determined by measuring the liquid flow rate out of each tube from the scale model. The scale model consisted of a tube assembly of 48 tubes arranged as shown in FIG. 7. Table 1 shows the liquid flow rates from each row of tubes expressed as a percentage of the total liquid at the inlet to the channel head.

Results of the experiments (see Table 1) show a significant improvement in distribution of the vapor/liquid flow across the inlet tubes of the tube sheet 24b using a flow distributor 50 as shown and described herein. Applicants' invention is more efficient, robust and can be implemented in existing alkylation reactors with little cost and risk, particularly since vanes and baffles are not involved.

TABLE 1

| Tube Row | Liquid Flow [% based on total liquid] | |
| --- | --- | --- |
| | Applicants' Invention | Prior Art |
| A | 20.9 | 31.0 |
| B | 18.6 | 14.6 |
| C | 14.1 | 13.3 |
| D | 15.4 | 6.6 |
| E | 18.0 | 3.1 |
| F | 13.0 | 31.4 |

What we claim is:

1. An alkylation reactor comprising a shell having a channel head, said channel head having an inlet nozzle and an outlet nozzle separated by a partition, a tube sheet mounted transversely of said shell for mounting thereon a plurality of u-shaped tubes wherein said tubes traverse the length of said reactor shell from the inlet side of said channel head and make a U-turn to the outlet side of said channel head, the improvement comprising:

a flow distributor mounted within the inlet side of said channel head for uniformly distributing, over the inlet side of said tube sheet, any fluid entering said inlet side of said channel head, said flow distributor having an inlet side for sealingly surrounding said inlet nozzle of said inlet side of said channel head, said flow distributor being a diverging horn-shaped duct adapted to turn said fluid flow from said inlet direction toward the tube sheet and toward the input side of said tubes and further including a trip ring mounted on the inlet side of said flow distributor for dislodging any liquid flow on the inside of said inlet.

2. The apparatus of claim 1 further including:

a plurality of windows cut into the wall of said inlet side of said flow distributor around its circumference and immediately downstream of said trip ring for aspirating any liquid accumulating in the channel head.

3. The apparatus of claim 2 further including:

a trip bar rigidly mounted to the top of the inside surface of said flow distributor for dislodging any liquid film flowing on the roof of said distributor.

4. A heat exchanger comprising a shell having a channel head, said channel head having an inlet nozzle and an outlet nozzle separated by a partition, a tube sheet mounted transversely of said shell for mounting thereon a plurality of tubes wherein said tubes traverse the length of said reactor shell from the inlet side of said channel head to an outlet channel head, the improvement comprising:

a flow distributor mounted within the inlet channel head for uniformly distributing, over the inlet side of said tube sheet, any fluid entering said inlet side of said channel head, said flow distributor having an inlet side for sealingly surrounding said inlet nozzle of said inlet side of said channel head, said flow distributor being a diverging horn-shaped duct adapted to turn said fluid flow from said inlet direction toward the tube sheet and toward the input side of said tubes and further including a trip ring mounted on the inlet side of said flow distributor for dislodging any liquid flow on the inside of said inlet nozzle.

5. The apparatus of claim 4 further including:

a plurality of windows cut into the wall of said inlet side of said flow distributor around its circumference and immediately downstream of said trip ring for aspirating any liquid accumulating in the channel head.

6. The apparatus of claim 5 further including:

a trip bar rigidly mounted to the top of the inside surface of said flow distributor for dislodging any liquid film flowing on the roof of said distributor.

7. A method for uniformly distributing liquid flow across the tube sheet of an alkylation reactor comprising the steps of:

directing a liquid flow into the inlet channel head of an alkylation reactor;

placing a trip ring at said inlet of said alkylation reactor;

dislodging any liquid film by means of said trip ring;

changing the direction of said liquid flow by approximately 90 degrees inside said reactor inlet channel head;

directing said liquid flow into a horn whose cross-section changes from that of the inlet to approximately that of said tube sheet;

placing a protrusion on the interior of said horn near the outlet of said horn;

forcing said liquid flow to diverge while changing its flow direction by means of said protrusion; and directing said liquid flow uniformly over said inlet side of said tube sheet.

8. A method for uniformly distributing liquid flow across the tube sheet of a heat exchanger comprising the steps of:

directing a liquid flow into the inlet of a heat exchanger;

placing a trip ring at said inlet of said heat exchanger;

dislodging any liquid film by means of said trip ring;

changing the direction of said liquid flow by approximately 90 degrees inside said heat exchanger inlet;

directing said liquid flow into a horn whose cross-section changes from that of the inlet to approximately that of said tube sheet;

placing a protrusion on the interior of said horn near the outlet of said horn;

forcing said liquid flow to diverge while changing its flow direction by means of said protrusion; and directing said liquid flow uniformly over said inlet side of said tube sheet.

* * * * *